US007004170B1

(12) United States Patent
Gillstrom

(10) Patent No.: US 7,004,170 B1
(45) Date of Patent: Feb. 28, 2006

(54) OXYGEN CANNULA

(76) Inventor: Jim A. Gillstrom, 21137 W. Walnut La., Plainfield, IL (US) 60544

( * ) Notice: Subject to any disclaimer, the term of this patent is extended or adjusted under 35 U.S.C. 154(b) by 0 days.

(21) Appl. No.: 11/056,772

(22) Filed: Feb. 11, 2005

(51) Int. Cl.
*A61M 16/00* (2006.01)
*A61M 15/08* (2006.01)
*A62B 18/08* (2006.01)

(52) U.S. Cl. .......................... 128/207.18; 128/206.11; 128/207.11

(58) Field of Classification Search .......... 128/206.27, 128/207.14, 207.15, 207.11, 207.18, DIG. 26, 128/206.11, 207.17, 202.27; 607/139–140; 2/171, 171.5, 172, 173, 209.13
See application file for complete search history.

(56) References Cited

U.S. PATENT DOCUMENTS

| 804,272 | A | | 11/1905 | Schwartz |
| 2,763,263 | A | | 9/1956 | Ellman |
| 2,931,358 | A | * | 4/1960 | Sheridan ................ 128/207.18 |
| 3,513,844 | A | | 5/1970 | Smith |
| 3,802,431 | A | | 4/1974 | Farr |
| 4,282,871 | A | | 8/1981 | Chodorow et al. |
| 4,406,283 | A | | 9/1983 | Bir |
| 4,422,456 | A | | 12/1983 | Tiep |
| 4,739,757 | A | | 4/1988 | Edwards |
| 4,836,200 | A | | 6/1989 | Clark |
| 4,915,104 | A | | 4/1990 | Marcy |
| 4,915,105 | A | * | 4/1990 | Lee ........................ 128/205.27 |
| 4,995,384 | A | | 2/1991 | Keelling |
| 5,117,818 | A | | 6/1992 | Palfy |
| 5,269,296 | A | * | 12/1993 | Landis .................. 128/207.18 |
| 5,438,979 | A | | 8/1995 | Johnson, Jr. et al. |
| 5,636,630 | A | | 6/1997 | Miller et al. |
| 5,645,058 | A | | 7/1997 | Odom |
| 6,298,850 | B1 | | 10/2001 | Agraves |
| 6,536,436 | B1 | * | 3/2003 | McGlothen ............ 128/207.18 |
| 6,684,883 | B1 | | 2/2004 | Burns |
| 2004/0025884 | A1 | | 2/2004 | McKown |

FOREIGN PATENT DOCUMENTS

FR 2725905 10/1994

OTHER PUBLICATIONS

Dinesen, Timothy PhD MBA, A Comparison of the OxyArm Oxygen Delivery Device and Standard Nasal Cannulae In Chronic Obstructive Pulmonary Disease Patients, Respiratory Care, Feb. 2003, pp. 120-123, vol. 28 No. 2, Health Science Libraries, University of Washington.

Ling, Elizabeth, The OxyArm- a new minim contact oxygen delivery system for mouth or nosebreathing, Canadian Journal of Anesthesia, 2002, pp. 297-392, vol. 49 No. 3.

* cited by examiner

Primary Examiner—Teena Mitchell
(74) Attorney, Agent, or Firm—Beem Patent Law Firm

(57) ABSTRACT

An oxygen cannula has an oxygen inlet flowably connectable to an oxygen supply, two neck tubes each flowably connectable to the oxygen inlet, two oxygen delivery each having a tube end and an oxygen outlet, wherein each one of the tube ends is flowably connectable to a corresponding neck tube and each of the oxygen outlets delivers oxygen to a patient, and a harness extending behind the patient's neck, wherein the harness has two ends connectable to the corresponding neck tubes, and wherein the harness absorbs force exerted to the oxygen inlet. In one aspect, there are two oxygen delivery tubes and each has an output end that flowably connects to a corresponding end on a nostril feed having two nostril inserts, wherein the two nostril inserts deliver oxygen into a patient's nostrils. In another aspect, an adjuster secures the oxygen delivery tubes behind the patient's head and the nasal inserts are securely positioned within the patient's nostrils.

8 Claims, 2 Drawing Sheets

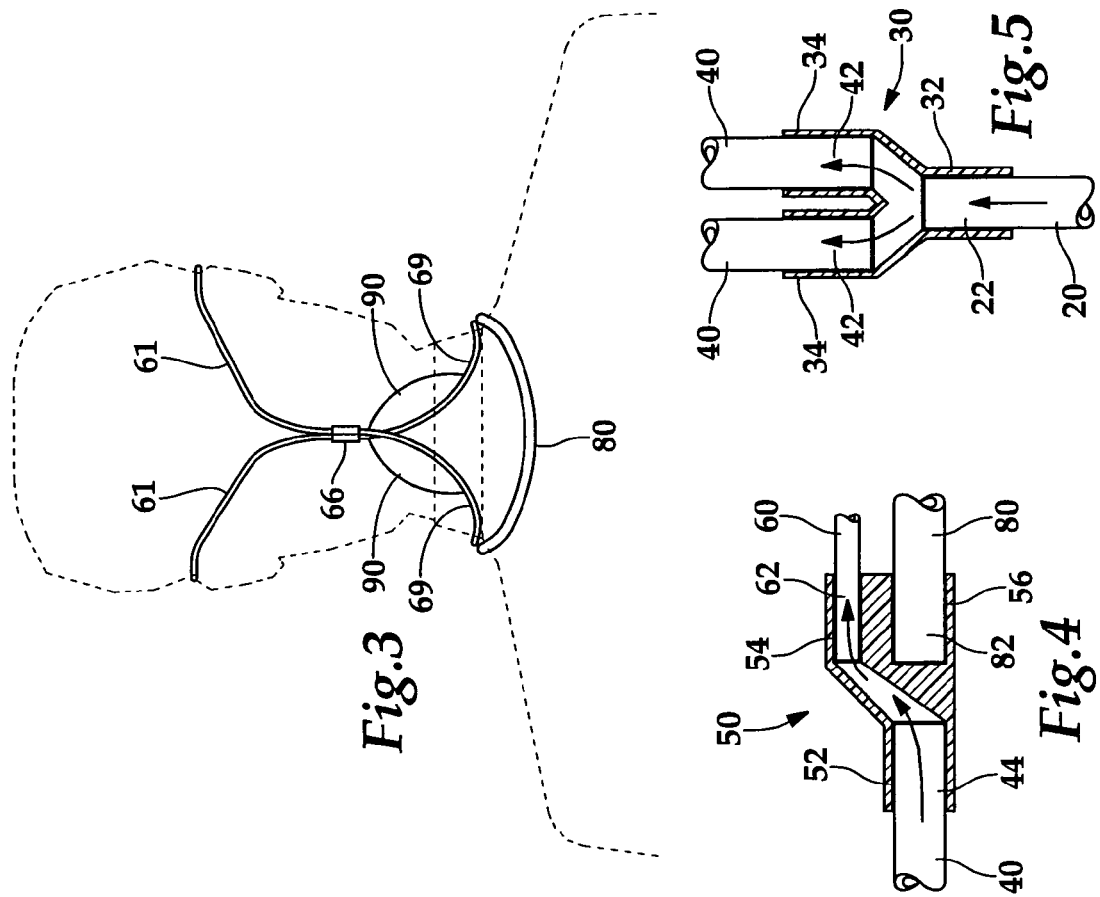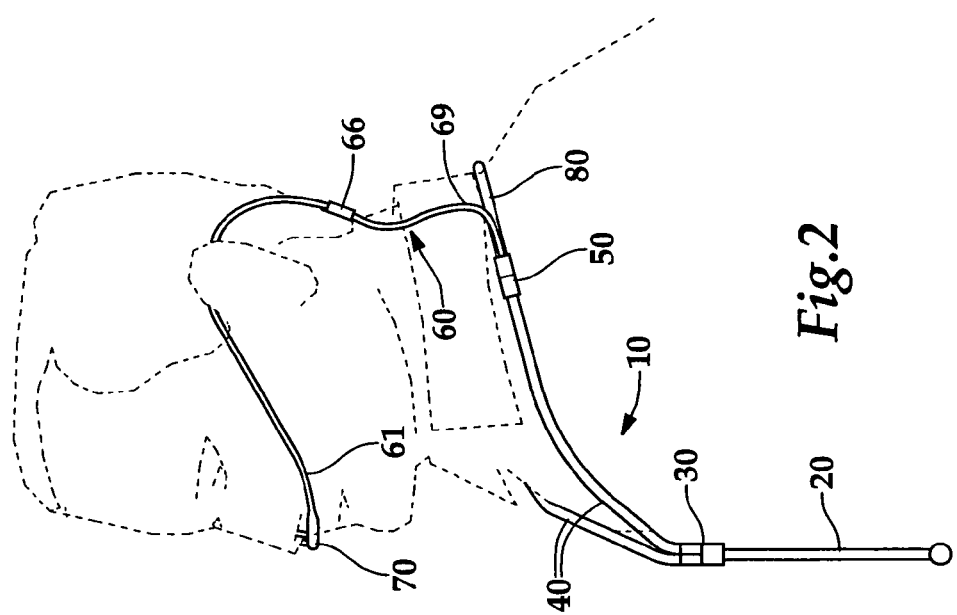

OXYGEN CANNULA

BACKGROUND

1. Field of the Invention

This invention is directed generally to oxygen cannulas, and directed more specifically to an oxygen cannula that directs force exerted on an oxygen inlet to the wearer's neck area.

2. Description of the Prior Art

When a physician prescribes oxygen therapy for a patient, an oxygen cannula is part of the usual equipment chosen for the inhalation protocol. Oxygen cannulas are designed to deliver oxygen from an oxygen source, usually a concentrator or a tank, to the nostrils at the prescribed rate determined by the healthcare giver. The typical oxygen cannula is attached to the patient's face by inserting the nasal tips into the patient's nostrils and passing the cannula tubing over and around both ears. The typical oxygen cannula includes an adjuster under the patient's chin for tightening the cannula tubing to the head region. The other end of the oxygen cannula is connectable to an oxygen source. Usually, the oxygen cannula is connectable to a tube that is connected to the oxygen source.

When a patient wearing an oxygen cannula moves around, the oxygen tube (to which the cannula is attached) can catch on furniture and doors, or be stepped on by feet. In this situation, the patient experiences extreme tugging on the ears because of the oxygen cannula tubes passing over and around the ears, which results in discomfort as well as irritation to the skin behind the ears. The typical cannula transfers the force from any agitation to the oxygen tube directly to the patient's ears and nose.

Some neck supports for oxygen cannulas attempt to minimize the discomfort to the ears, but the neck supports are typically separate lanyards that must be attached to an oxygen cannula, as shown in U.S. Pat. No. 4,915,104. The lanyard clamps to the oxygen cannula by a C-clamp and the C-clamp may crush the cannula tubes and impede the flow of oxygen. Moreover, patients may have difficulty adjusting the length of the lanyard to properly position the oxygen cannula.

A typical neck support, shown in U.S. Pat. No. 6,536,436 has two ends that loosely loop around the oxygen cannula tubes, but allow the tubes to slide within the loops. This type of neck support will still transfer any force exerted on the oxygen inlet to the cannula tubes leading up to the patient's ears and nose. More problematically, this type of neck support might flatten the oxygen cannula tubes carrying the oxygen to the patient's nostrils when force is exerted on the oxygen inlet because the cannula tubes will be pulled against the loops of the neck support.

What is needed is an oxygen cannula having a harness that is easy to wear and that will not crush the oxygen cannula tubes while absorbing the force exerted on the oxygen inlet.

SUMMARY

An oxygen cannula has an oxygen inlet with a first end and a second end, wherein the first end is flowably connectable to an oxygen supply, two neck tubes each having a throat end and neck end, wherein the throat end is flowably connectable to a second end, two oxygen delivery tubes, each with a tube end and two an oxygen outlet, wherein each one of the delivery ends is flowably connectable to a corresponding neck end and each of the oxygen outlets delivers oxygen to a patient, and a harness extending behind the patient's neck, wherein the harness has two harness ends, each harness end being fixably connectable to each of the neck tubes, wherein no oxygen flows through the harness, and wherein the harness absorbs force exerted to the oxygen inlet. In one aspect, there are two oxygen delivery tubes and each has an output end that flowably connects to a corresponding end on a nostril feed having two nostril inserts. In another aspect, an adjuster secures the oxygen delivery tubes behind the patient's head and the nasal inserts are securely positioned within the patient's nostrils.

In a further aspect, the oxygen cannula has two tees, each one of the tees having an attaching prong, a delivery prong, and a harness prong, wherein each attaching prong is flowably connectable to a corresponding one of the neck ends, each delivery prong is flowably connectable to a corresponding one of the delivery ends, and each harness prong is connectable to a corresponding one of the harness ends. In still further aspects, the harness is made of quarter inch plastic tubing and the harness has a length of about ten inches. The harness is made of flexible material that does not substantially stretch in length.

BRIEF DESCRIPTION OF THE DRAWINGS

FIG. 2 is a side view of a patient wearing an oxygen cannula.

FIG. 3 is a rear view of a patient wearing an oxygen cannula.

FIG. 4 is a side view of a tee connecting an oxygen delivery tube, a neck tube, and a harness.

FIG. 5 is a side view of a source splitter connecting an oxygen inlet to a pair of neck tubes.

DETAILED DESCRIPTION OF THE INVENTION

Figure 1:
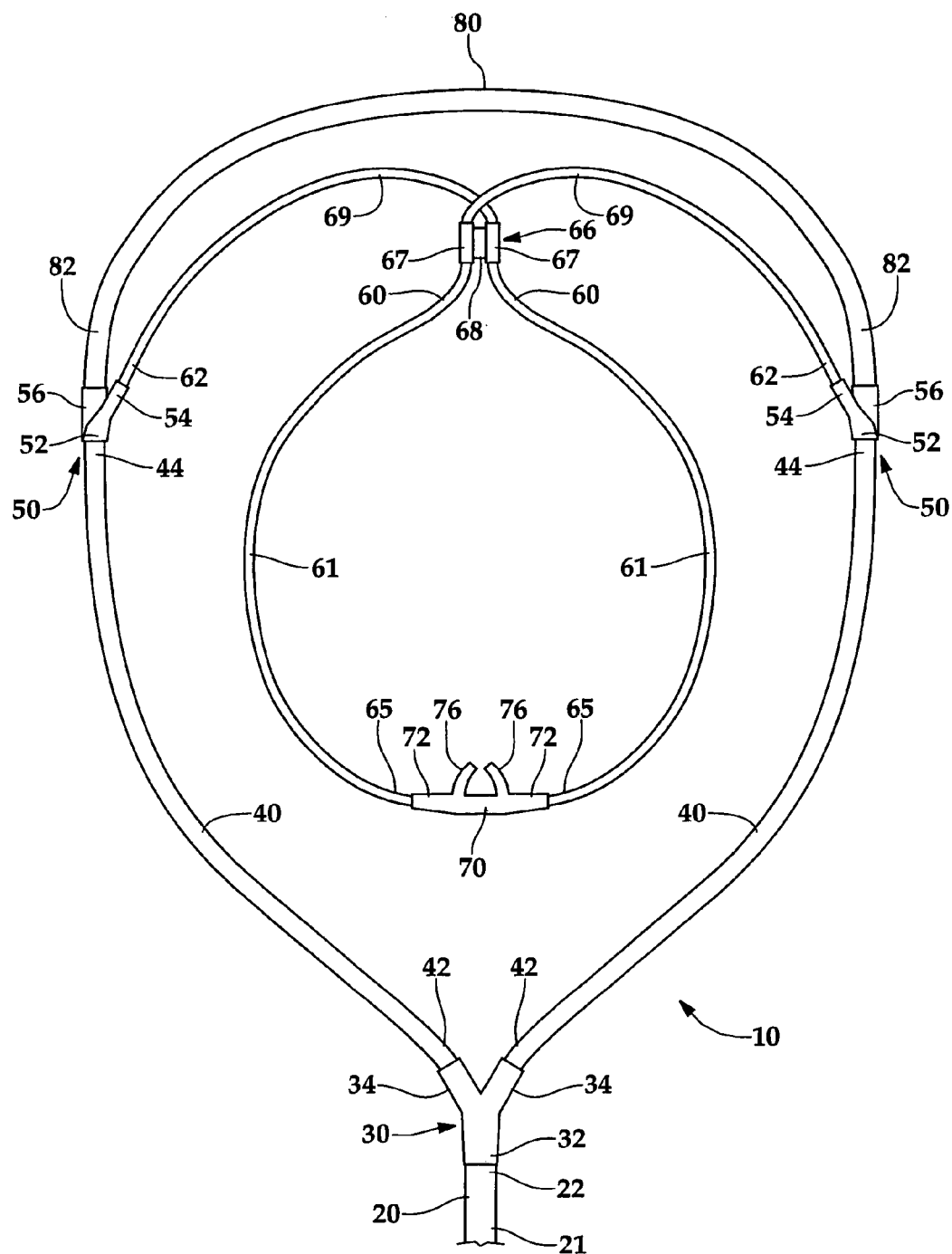
FIG. 1 is a perspective view of an oxygen cannula.

Oxygen cannula 10 has oxygen inlet 20 flowably connectable to two corresponding neck tubes 40, which flowably connect to corresponding oxygen delivery tubes 60 to deliver oxygen to a patient's nostrils, and harness 80 connects to each neck tube 40 to absorb force exerted on oxygen inlet 20.

Oxygen cannula 10 is a two stage device to hold the cannula comfortably to a patient's neck and head region, and to deliver oxygen to a patient's nostrils. Stage one holds oxygen cannula 10 to a wearer's neck and absorbs force exerted on oxygen inlet 20. Stage two delivers oxygen to the nostrils through oxygen delivery tubes 60. Oxygen cannula 10 has oxygen inlet 20 with first end 21 connectable to an oxygen source. Oxygen inlet 20 then delivers oxygen to neck tubes 40, and then to delivery tubes 60, and then to oxygen outlets 75 and into the patient's nostrils. Harness 80 is connectable to neck tubes 40. Harness 80 extends around the back of the patient's neck and is blocked so that no oxygen flows through harness 80.

During stage one, oxygen cannula 10 is held and positioned comfortably in place on the patient's neck. Stage one is accomplished mainly with oxygen inlet 20, neck tubes 40 and harness 80, as seen in FIGS. 1 and 3.

As shown in FIG. 1, oxygen cannula 10 has oxygen inlet 20 having first end 21 connectable to an oxygen source, e.g. an oxygen tank or an oxygen compressor, and second end 22 connectable to source splitter 30. In a preferred embodiment, oxygen inlet 20 is made of hollow plastic tubing and is preferably between about ⅛ inch and about ½ inch in diameter, more preferably between about 3/16 of an inch and about 5/16 inch in diameter, and still more preferably about 1/4 of an inch in diameter.

As shown in FIG. 5, source splitter 30 is a hollow Y-shaped plastic piece with three prongs: one input prong 32 and two output prongs 34. Input prong 32 is connected to second end 22 of oxygen inlet 20 so that oxygen can flow from oxygen inlet 20 to input prong 32. In a preferred embodiment, input prong 32 has a larger diameter than second end 22 and forms an air tight seal with the outside of oxygen inlet 20 at second end 22. The seal between input prong 32 and second end 22 can be made by methods known in the art.

As shown in FIG. 1, one neck tube 40 connects to each output prong 34. Each neck tube 40 has throat end 42 and neck end 44. Each throat end 42 is connected to one output prong 34 so that oxygen can flow from output prong 34 into throat end 42. In a preferred embodiment, output prong 34 has a larger diameter than throat end 42 and forms an air tight seal with the outside of neck tube 40 at throat end 42. The seal between output prong 34 and throat end 42 can be made by methods known in the art. In one embodiment, neck tube 40 is made of hollow plastic tubing and is preferably between about 8 inches and 14 inches in length, more preferably between about 9 inches and about 12 inches in length, and most preferably about 10 inches in length. Neck tube 40 is preferably between about 1/8 and about 1/2 inch in diameter, more preferably between about 3/16 of an inch and about 5/16 inch in diameter, and still more preferably about 1/4 of an inch in diameter.

As shown in FIG. 4, tee 50 is hollow and has three prongs, attaching prong 52, delivery prong 54 and harness prong 56. Each neck end 44 is connected to corresponding attaching prong 52 so that oxygen can flow from neck end 44 through attaching prong 52. In a preferred embodiment, attaching prong 52 has a larger diameter than neck end 44 and fits over neck end 44 to form an air tight seal with the outside of neck end 44.

As shown in FIG. 2, harness 80 helps position oxygen cannula 10 by keeping neck tubes 40 in place on the patient's chest and throat area. Also, when the oxygen source tube connecting oxygen inlet 20 to the oxygen source is caught on furniture or trampled underfoot, harness 80 absorbs the force.

Harness 80 lies behind a patient's neck and has two harness ends 82, each connected to harness prong 56. In a preferred embodiment, oxygen is blocked from entering harness 80 at either harness prong 56 or harness ends 82. In a preferred embodiment, harness 80 is between about 8 inches and about 14 inches in length, more preferably between about 9 inches and about 12 inches in length, and most preferably about 10 inches in length. In one embodiment, harness 80 is made from plastic tubing preferably between about 1/8 inch and about 1/2 inch in diameter, more preferably between about 3/16 inch and 5/16 inch in diameter, and still more preferably about 1/4 inch in diameter.

In stage two, oxygen cannula 10 delivers oxygen from an oxygen tank to a patient's nostrils. As shown in FIG. 1, oxygen cannula 10 has oxygen inlet 20 with one end connectable to an oxygen tank so that oxygen flows from the oxygen tank to oxygen inlet 20. Oxygen inlet 20 feeds into neck tubes 40 and which in turn feed into oxygen delivery tubes 60 which have two oxygen outlets 65. In one embodiment oxygen outlets 65 connect to nostril feed 70 which has two nostril inserts 76. In one embodiment (not shown), oxygen outlets 65 may be nostril inserts 76.

Two oxygen delivery tubes 60 each have a tube end 62 and an oxygen end 65. Each end 62 is connected to delivery prong 54 on tee 50 so that oxygen can flow from delivery prong 54 to tube ends 62. As shown in FIG. 4, in a preferred embodiment, delivery prong 54 has a larger diameter than tube ends 62 and forms an air tight seal with the outside of oxygen delivery tube 60 at tube ends 62. Oxygen delivery tube 60 is preferably between about 1/16 inch and 1/4 inch in diameter, and more preferably about one eighth of an inch in diameter.

Oxygen delivery tubes 60 extends upwardly from delivery prong 54 toward the back of a patient's head, as shown in FIG. 2. Oxygen delivery tubes 60 fits over a patient's ears and passes in front of a patient's face so that oxygen outlets 75 are positioned in front of a patient's face. Oxygen delivery tubes 60 preferably have a length of between about 15 inches and about 20 inches, more preferably between about 16 inches and about 19 inches, and most preferably about 18 inches.

In one embodiment, oxygen cannula 10 may have nostril feed 70 connected to oxygen ends 65. Nostril feed 70 is a hollow plastic tube between about 1/8 of an inch and about 1/2 inch in diameter, and more preferably between about 1/4 inch and about 3/8 inch in diameter. Nostril feed 70 is preferably between about 1 inch and 3 inches in length, and more preferably between about 2 inches and 3 inches in length. Nostril feed 70 may have two nostril inserts 76 which may be spaced and curved to best fit within a patient's nostrils. In this embodiment, nostril inserts 76 are the oxygen outlets. Nostril feed 70 has two connection ends 72. Connection ends 72 are preferably of larger diameter than oxygen ends 65 and form an air tight scale with the outside of oxygen delivery tube 60 at oxygen ends 65.

As seen in FIGS. 2 and 3, adjuster 66 tightens oxygen delivery tubes 60 to a patient's head so that nostril inserts 76 will not fall out of a patient's nostrils. Adjuster 66 typically resides on the back of a patient's head and slides an oxygen delivery tubes 60 to adjust the length of oxygen delivery tubes 60 passing over a patient's ears and in front of a patient's face.

Length 61 measures the length of oxygen delivery tube 60 from adjuster 66 to nostril feed 70. Sliding adjuster 66 towards the top of a patient's head shortens length 68. Portion 69 lies below adjuster 66 and hangs slack at dorsal side of a patient's head. Preferably, delivery tubes 60 cross over each other as they extend upwardly from delivery prongs 54 as seen in FIG. 3. Below adjuster 66, delivery tubes 60 preferably cross to increase angle 90 of delivery tubes 60 as delivery tubes 60 extends upwardly from a patient's neck area. If angle 90 is too small, delivery tubes 60 may be forced by adjuster 66 to bend too sharply and thereby impede the flow of oxygen. Delivery tube 60 that cross over below adjuster 66 may increase angle 90 and decrease the likelihood of adjuster 66 causing delivery tubes 60 to bend to sharply and impede the flow of oxygen to nostril feed 70.

Friction between adjuster 66 and oxygen delivery tube 60 keeps adjuster 60 in a desired position on oxygen delivery tube 60 when no force is exerted on adjuster 66. In a preferred embodiment, adjuster 66 may be hollow cylinder 67. Cylinder 67 may fit over oxygen delivery tubes 60 so that there is contact between cylinder 67 and oxygen delivery tubes 60. In one embodiment adjuster may include two cylinders 67 connected by area 68.

As seen in FIGS. 2 and 3, portion 69 of oxygen delivery tubes 60, positioned under adjuster 66, lies slack against the dorsal side of a patient's head. Portion 69 should not be displaced significantly when force is exerted upon oxygen inlet 20, due to absorption by harness 80. A little force exerted upon oxygen inlet 20 may be transferred to portion 69, but the slack in portion 69 will absorb the transferred force. A patient's ears and nose should feel little to no impact from the force exerted upon oxygen inlet 20.

Without harness 80, when oxygen inlet 20 is caught on furniture on underfoot, the force exerted on oxygen inlet 20 may be transferred to oxygen delivery tubes 60, and a patient's ears and nose may feel the brunt of the force. Harness 80 absorbs the force and prevents discomfort to a patient's ears and nose.

With harness 80 in place on oxygen cannula 10, all of the force exerted on neck tubes 40 from oxygen inlet 20 will be transferred to harness 80 and felt on the dorsal side of a patient's neck. Harness 80 is a predetermined length and preferably made of a material that will not extend significantly when encountering the force of oxygen inlet 20 getting caught. Oxygen delivery tubes 60 should not be displaced when force is exerted to oxygen inlet 20. Most of the force transferred to harness 80 will be transferred to the patient's neck instead of a patient's ears and nose through oxygen delivery tubes 60.

Oxygen cannula 10 accomplishes the stage one goal of holding oxygen cannula 10 comfortably in place so that the stage two goal of delivering oxygen to the patient's nostrils can be met with minimal to no discomfort to the patient. Harness 80 absorbs agitation to oxygen inlet 20 and makes wearing oxygen cannula 10 more bearable so that the patient can receive oxygen therapy comfortably and conveniently.

Oxygen cannula 10 has oxygen inlet 20 with first end 21 and second end 22, wherein first end 21 is flowably connectable to an oxygen supply, two neck tubes 40 each having throat end 42 and neck end 44, wherein each throat end 42 is flowably connectable to second end 22. The oxygen cannula also has oxygen delivery tubes 60 each having a tube end 62 and an oxygen outlet, wherein each one of delivery ends 62 is flowably connectable to a corresponding one of the neck ends 44 and each of oxygen outlets 75 delivers oxygen to a patient. Oxygen cannula 10 further has harness 80 extending behind the patient's neck, wherein harness 80 has two harness ends 82, each harness end 82 being fixedly connectable to each one of corresponding neck tubes 40, wherein no oxygen flows through harness 80, and wherein harness 80 absorbs force exerted to oxygen inlet 20. Oxygen delivery tubes 60 fits over the patient's ears. Two oxygen delivery tubes 40 each has an output end 65, wherein each output end 65 flowably connects to a corresponding end on nostril feed 70 having two nostril inserts 76.

Oxygen cannula 10 further has two tees 50, each of the tees having an attaching prong 52, a delivery prong 54, and a harness prong 56, wherein each attaching prong 52 is flowably connectable to a corresponding one of neck ends 44, each delivery prong 54 is flowably connectable to a corresponding one of delivery ends 62, and each harness prong 56 is connectable to corresponding harness end 82. Harness 80 may be made of quarter inch plastic tubing and has a length of about ten inches. Harness 80 comprises flexible material that does not substantially stretch in length.

Although this invention has been described above with reference to particular means, materials and embodiments, it is to be understood that the invention is not limited to these disclosed particulars, but extends instead to all equivalents within the scope of the following claims.

We claim:

1. An oxygen cannula comprising:
   an oxygen inlet with a first end and a second end, wherein said first end is flowably connectable to an oxygen supply;
   two neck tubes, each having a throat end and a neck end, wherein each said throat end is flowably connectable to said second end;
   two oxygen delivery tubes, each having a tube end and an oxygen outlet, wherein each one of said tube ends is flowably connectable to a corresponding said neck end and each of said oxygen outlets delivers oxygen to a patient;
   a harness extending behind said patient's neck, wherein said harness has two harness ends, each harness end being fixedly connectable to one of said neck tubes, wherein no oxygen flows through said harness, and wherein said harness absorbs force exerted upon said oxygen inlet.

2. An oxygen cannula according to claim 1, wherein said oxygen delivery tube fits over said patient's ears.

3. An oxygen cannula according to claim 1, further comprising a nostril feed having two nostril insets and two oxygen delivery tubes each having an output end, wherein each of said output end flowably connects to a corresponding end on said nostril feed.

4. An oxygen cannula according to claim 3, wherein an adjuster secures said oxygen delivery tubes behind said patient's head and said nasal inserts are securely positioned within said patient's nostrils.

5. An oxygen cannula according to claim 1, wherein said harness comprises quarter inch plastic tubing.

6. An oxygen cannula according to claim 1, wherein said harness has a length of about ten inches.

7. An oxygen cannula according to claim 1, wherein said harness comprises flexible material that does not substantially stretch in length.

8. An oxygen cannula comprising:
   an oxygen inlet with a first end and a second end, wherein said first end is flowably connectable to an oxygen supply;
   two neck tubes each having a throat end and a neck end, wherein each said throat end is flowably connectable to said second end;
   two oxygen delivery tubes, each having a tube end and an oxygen outlet, wherein each one of said tube ends is flowably connectable to corresponding said neck end and each of said oxygen outlets delivers oxygen to a patient;
   a harness extending behind said patient's neck, wherein said harness has two harness ends, each harness end being fixedly connectable to each of said neck tubes, wherein no oxygen flows through said harness, and wherein said harness absorbs force exerted to said oxygen inlet, and
   two tees, each one of said tees having an attaching prong, a delivery prong, and a harness prong, wherein each said attaching prong is flowably connectable to a corresponding one of said neck ends, each delivery prong is flowably connectable to a corresponding one of said delivery ends, and each said harness prong is connectable to a corresponding one of said harness ends.

* * * * *